US011872077B2

(12) United States Patent
Miyachi et al.

(10) Patent No.: US 11,872,077 B2
(45) Date of Patent: Jan. 16, 2024

(54) ULTRASOUND DIAGNOSTIC SYSTEM AND METHOD OF CONTROLLING ULTRASOUND DIAGNOSTIC SYSTEM

(71) Applicant: FUJIFILM Corporation, Tokyo (JP)

(72) Inventors: Yukiya Miyachi, Ashigara-kami-gun (JP); Tomoki Inoue, Ashigara-kami-gun (JP)

(73) Assignee: FUJIFILM Corporation, Tokyo (JP)

( * ) Notice: Subject to any disclaimer, the term of this patent is extended or adjusted under 35 U.S.C. 154(b) by 467 days.

(21) Appl. No.: 16/299,964

(22) Filed: Mar. 12, 2019

(65) Prior Publication Data
US 2019/0209121 A1 Jul. 11, 2019

Related U.S. Application Data

(63) Continuation of application No. PCT/JP2017/016546, filed on Apr. 26, 2017.

(30) Foreign Application Priority Data

Sep. 12, 2016 (JP) ................. 2016-177816

(51) Int. Cl.
A61B 8/08 (2006.01)
A61B 8/14 (2006.01)
(Continued)

(52) U.S. Cl.
CPC .......... *A61B 8/0858* (2013.01); *A61B 8/0891* (2013.01); *A61B 8/14* (2013.01);
(Continued)

(58) Field of Classification Search
CPC ....... A61B 8/0858; A61B 8/0891; A61B 8/14; A61B 8/4488; A61B 8/461; A61B 8/463;
(Continued)

(56) References Cited

U.S. PATENT DOCUMENTS 5,660,179 A * 8/1997 Matsumoto .............. A61B 8/08
600/440
6,213,945 B1 4/2001 Tynan
(Continued)

FOREIGN PATENT DOCUMENTS

| CN | 102895457 A | 9/2012 |
| CN | 104885872 A | 6/2015 |

(Continued)

OTHER PUBLICATIONS

Translated Ogasawa (JP2010148566A) (Year: 2010).*
(Continued)

*Primary Examiner* — Katherine L Fernandez
*Assistant Examiner* — Brooke Lyn Klein
(74) *Attorney, Agent, or Firm* — Birch, Stewart, Kolasch & Birch, LLP

(57) ABSTRACT

An ultrasound diagnostic system includes an ultrasound diagnostic device that creates test images of an intima-media thickness of a blood vessel, a workstation connected to the ultrasound diagnostic device, and a database that sequentially stores the test images created by the ultrasound diagnostic device. The workstation includes an input unit for allowing a user to input various kinds of information, a display unit, a workstation control unit that retrieves test images in past tests for the patient as past images from the test images stored in the database to make the display unit display the past images stored in the database as thumbnails, after a current image that is a test image of a current test are created for the patient by the ultrasound diagnostic device, and a test report creation unit that automatically creates a test report on the basis of the current image, and at least one past image selected by the user via the input unit from the past images displayed as the thumbnails on the display unit.

16 Claims, 11 Drawing Sheets

(51) Int. Cl.
    *G16H 15/00*     (2018.01)
    *G16H 10/60*     (2018.01)
    *G16H 30/40*     (2018.01)
    *A61B 8/00*     (2006.01)

(52) U.S. Cl.
    CPC ............ *A61B 8/4488* (2013.01); *A61B 8/461* (2013.01); *A61B 8/463* (2013.01); *A61B 8/485* (2013.01); *A61B 8/5223* (2013.01); *G16H 10/60* (2018.01); *G16H 15/00* (2018.01); *G16H 30/40* (2018.01)

(58) Field of Classification Search
    CPC ...... A61B 8/485; A61B 8/5223; G16H 10/60; G16H 15/00; G16H 30/40
    See application file for complete search history.

(56) References Cited

U.S. PATENT DOCUMENTS

| | | | |
|---|---|---|---|
| 2003/0199762 A1 | 10/2003 | Fritz et al. | |
| 2004/0116813 A1* | 6/2004 | Selzer | A61B 5/02007 600/467 |
| 2004/0204965 A1* | 10/2004 | Gueck | G16H 30/20 707/E17.026 |
| 2007/0073147 A1* | 3/2007 | Holladay | A61B 5/02007 382/128 |
| 2007/0127795 A1* | 6/2007 | Lau | G16H 30/20 382/128 |
| 2008/0193004 A1* | 8/2008 | Mine | A61B 6/5247 382/131 |
| 2008/0196506 A1 | 8/2008 | Satoh et al. | |
| 2010/0113930 A1* | 5/2010 | Miyachi | A61B 5/02007 600/443 |
| 2012/0083698 A1* | 4/2012 | Chono | A61B 5/02007 600/443 |
| 2012/0310086 A1 | 12/2012 | Fukumoto et al. | |
| 2013/0109970 A1* | 5/2013 | Higuchi | A61B 8/14 600/443 |
| 2014/0136627 A1 | 5/2014 | Liang et al. | |
| 2014/0221836 A1* | 8/2014 | Takeda | A61B 8/463 600/443 |
| 2014/0276057 A1 | 9/2014 | Lee et al. | |
| 2014/0369583 A1 | 12/2014 | Toji et al. | |
| 2015/0356271 A1* | 12/2015 | Kozuka | H04N 21/4725 705/2 |
| 2017/0300620 A1* | 10/2017 | Rahme | G16H 30/20 |
| 2018/0000453 A1* | 1/2018 | Hunter | G06F 3/04883 |

FOREIGN PATENT DOCUMENTS

| | | | | |
|---|---|---|---|---|
| CN | 105243676 A | | 1/2016 | |
| FR | 2889757 A1 | | 2/2007 | |
| JP | 2005-390 A | | 1/2005 | |
| JP | 2008-194365 A | | 8/2008 | |
| JP | 2010-29481 A | | 2/2010 | |
| JP | 2010148566 | * | 7/2010 | ............... A61B 8/00 |
| JP | 2010-259529 A | | 11/2010 | |
| JP | 2012010734 A | * | 1/2012 | |
| JP | 2015-24132 A | | 2/2015 | |
| WO | WO 2006/038181 A1 | | 4/2006 | |
| WO | WO-2016080331 A1 | * | 5/2016 | ............. A61B 1/045 |

OTHER PUBLICATIONS

International Preliminary Report on Patentability and Written Opinion of the International Searching Authority (forms PCT/IB/373, PCT/ISA/237 and PCT/IB/326), dated Mar. 21, 2019, for corresponding International Application No. PCT/JP2017/016546 with a Written Opinion translation.

International Search Report (form PCT/ISA/210), dated Jul. 11, 2017, for corresponding International Application No. PCT/JP2017/016546, with an English translation.

Chinese Office Action and Search Report, dated Mar. 2, 2021, for corresponding Chinese Application No. 201780055657 X, with an English translation of the Chinese Office Action.

European Office Action, dated Apr. 22, 2021, for corresponding European Application No. 17848350.9.

Extended European Search Report, dated Jul. 30, 2019, for European Application No. 17848350.9.

Chinese Office Action for corresponding Chinese Application No. 201780055657.X, dated Dec. 3, 2021, with an English translation.

Chinese Office Action for corresponding Chinese Application No. 201780055657.X, dated May 6, 2022, with a partial English translation.

* cited by examiner

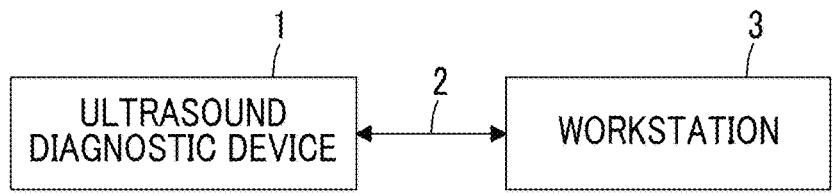
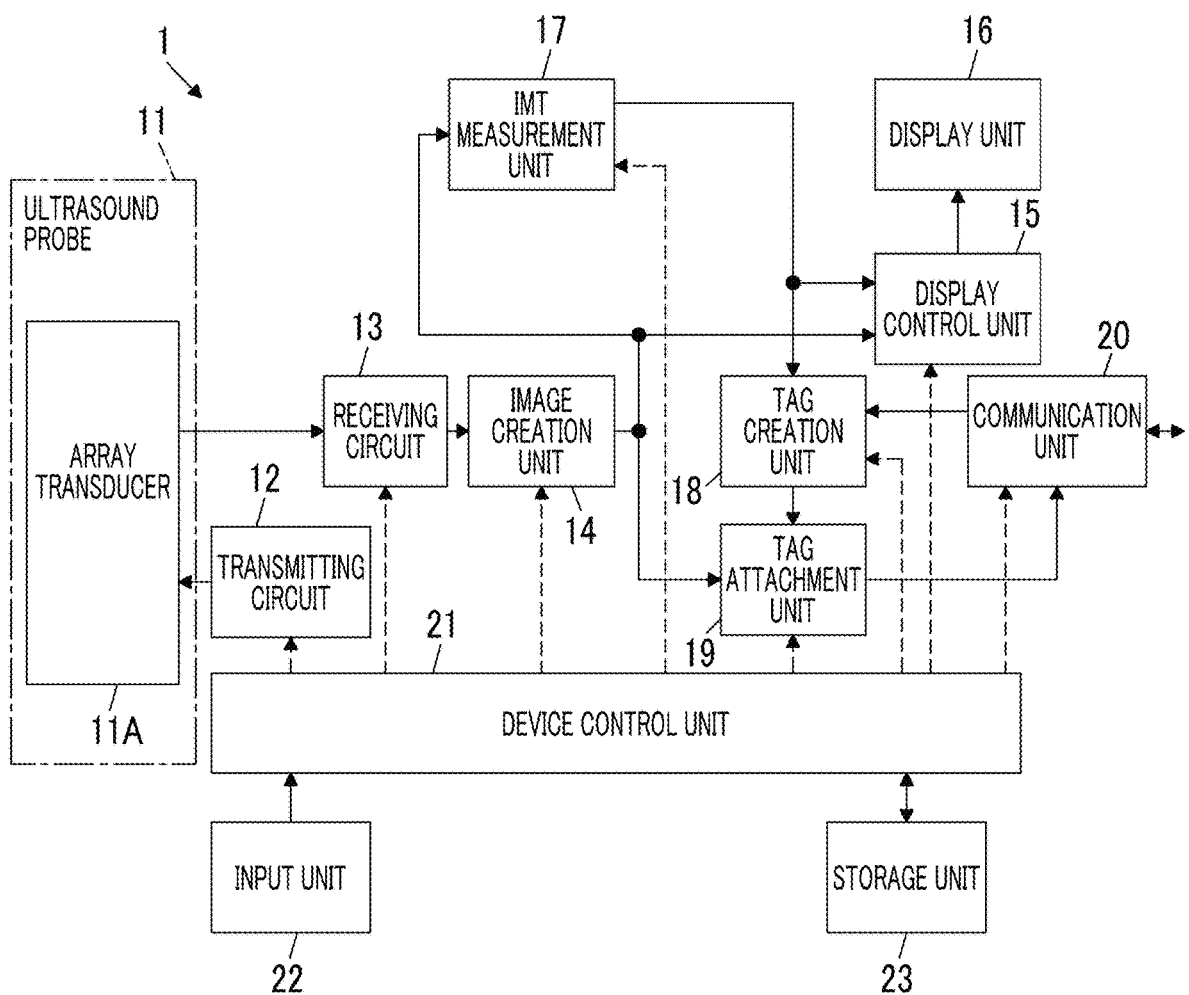

FIG. 11

| | | CURRENT TEST | PREVIOUS TEST | TEST BEFORE LAST |
|---|---|---|---|---|
| | TEST DATE | H26.7.10 | H23.7.9 | |
| | TEST PART | COMMON CAROTID ARTERY | COMMON CAROTID ARTERY | |
| RIGHT ARTERY | MAX IMT | 1.1 mm | 0.8 mm | |
| RIGHT ARTERY | PLAQUE | YES | NONE | |
| LEFT ARTERY | MAX IMT | 0.8 mm | 0.7 mm | |
| LEFT ARTERY | PLAQUE | YES | NONE | |

CAROTID ARTERY ECHO TEST REPORT

PATIENT ID: 0123456    SEX: FEMALE
PATIENT NAME: ○○ ○○    AGE: 62 YEARS OLD

R — report
F1 — patient info
F2 — test results table
F3 — graph (G)
F4 — test images
F5 — RESULTS OUTLINE: MAX IMT OF RIGHT CAROTID ARTERY IS 1.1 mm AND EXCEEDS REFERENCE RANGE. MAX IMT OF LEFT CAROTID ARTERY IS 0.8 mm AND IS WITHIN REFERENCE RANGE.
F6 — COMMENTS: THERE IS POSSIBILITY THAT ARTERIOSCLEROSIS MAY PROCEED. PLEASE PAY ATTENTION TO YOUR LIFESTYLE.

PUBLICATION DATE: H26.7.10

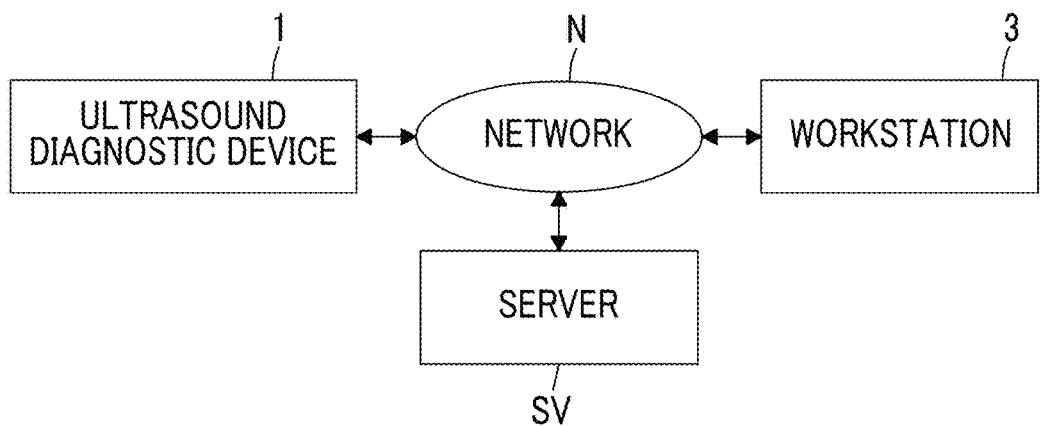
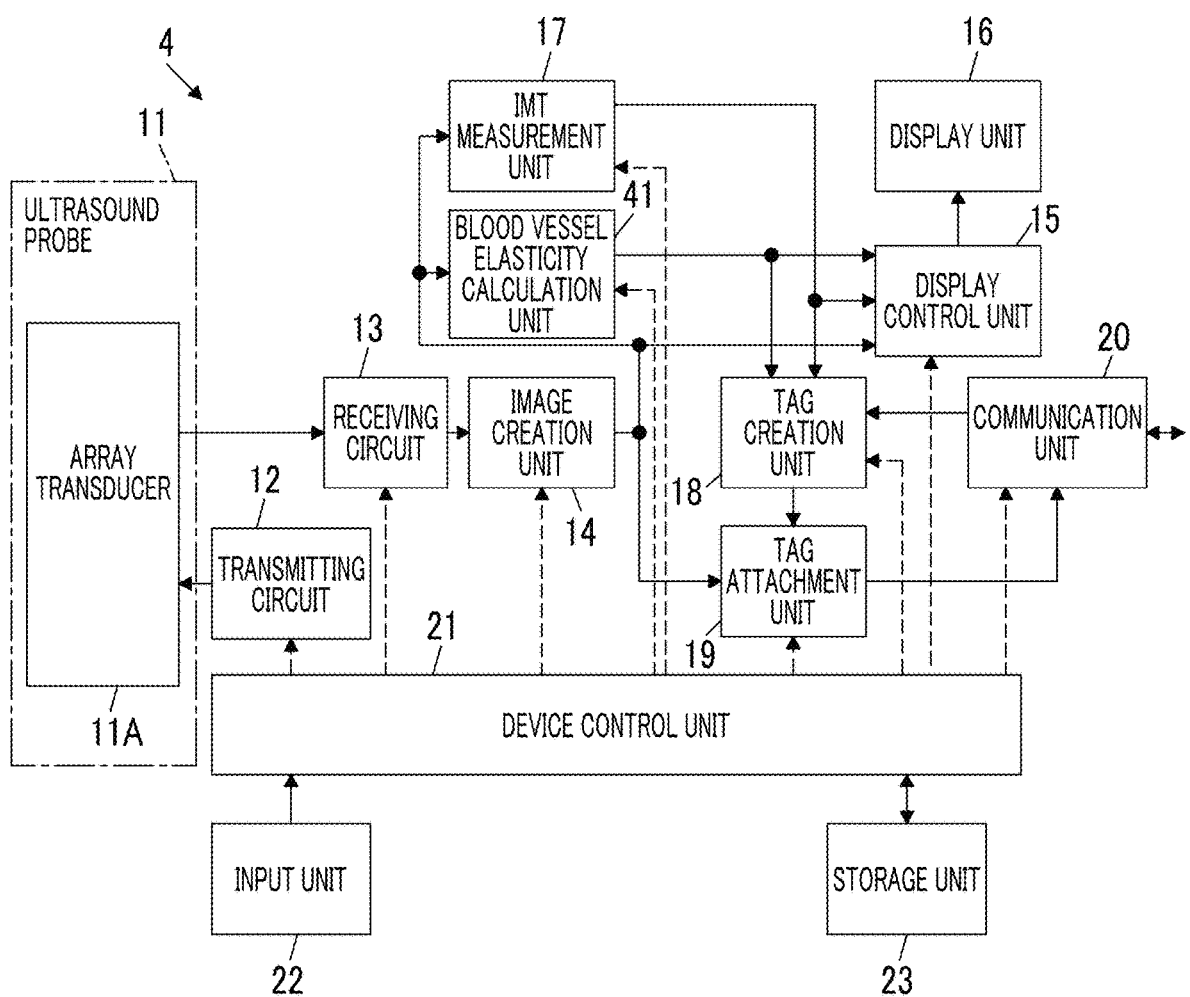

ULTRASOUND DIAGNOSTIC SYSTEM AND METHOD OF CONTROLLING ULTRASOUND DIAGNOSTIC SYSTEM

CROSS-REFERENCE TO RELATED APPLICATIONS

This application is a Continuation of PCT International Application No. PCT/JP2017/016546 filed on Apr. 26, 2017, which claims priority under 35 U.S.C. § 119(a) to Japanese Patent Application No. 2016-177816 filed on Sep. 12, 2016. The above application is hereby expressly incorporated by reference, in its entirety, into the present application.

BACKGROUND OF THE INVENTION

1. Field of the Invention

The present invention relates to an ultrasound diagnostic system and a method of controlling an ultrasound diagnostic system, and particularly, to an ultrasound diagnostic system that automatically creates a test report of an intima-media thickness of a blood vessel.

2. Description of the Related Art

In the medical field, ultrasound diagnostic devices using ultrasound images have been put to practical use. Generally, in this type of ultrasound diagnostic devices, a patient is scanned with an ultrasound beam from an ultrasound probe in which an array transducer is built, the ultrasound probe receives ultrasound echoes from the patient, and an ultrasound image is created by electrically processing received signals.

Additionally, in the ultrasound diagnostic devices, for example, in order to obtain information on circulatory organ system disease, such as arteriosclerosis, ultrasound waves can be transmitted and received toward a blood vessel, and an intima-media thickness (IMT) or the like of the blood vessel can be obtained on the basis of the obtained received signals. The value of this intima-media thickness varies with the progress of the circulatory organ system disease, such as arteriosclerosis, the state of the circulatory organ system disease, such as arteriosclerosis, can be estimated by monitoring the value. Thus, a user, for example, a doctor or a test engineer may explain diagnostic results of the circulatory organ system disease, such as arteriosclerosis while making the patient view test results of the intima-media thickness of the blood vessel. As a technique for performing such diagnosis, for example, JP2005-000390A discloses an ultrasound diagnostic device that creates a test image of the intima-media thickness of the blood vessel, and outputs a report showing this test image.

SUMMARY OF THE INVENTION

However, the report output by the ultrasound image diagnostic device disclosed in JP2005-000390A shows only a test image created in a test that is currently performed as the test image of the intima-media thickness. Therefore, secular changes in the same patient's intima-media thickness cannot be ascertained. Additionally, in order to ascertain the secular changes in the intima-media thickness of the same patient and to reflect test images of the intima-media thickness required in past tests in the report, the user has to retrieve past test results from a database or the like, substantial time and effort is taken, which may hinder quick diagnosis.

The invention has been made in order to solve such related-art problems, and an object thereof is to provide an ultrasound diagnostic system and a method of controlling an ultrasound diagnostic system that automatically create a test report that makes it possible to ascertain secular changes in the intima-media thickness of a blood vessel.

The ultrasound diagnostic system related to the invention is an ultrasound diagnostic system including an ultrasound diagnostic device that transmits an ultrasound beam toward a patient from an array transducer, receives an ultrasound echo from the patient, and creates a test image of an intima-media thickness of a blood vessel, and a workstation connected to the ultrasound diagnostic device. The ultrasound diagnostic system comprises a database that sequentially stores the test image created by the ultrasound diagnostic device. The workstation includes an input unit for allowing a user to input various kinds of information, a display unit, a workstation control unit that retrieves a test image in a past test for the patient as a past image from the test image stored in the database to make the display unit display the past image as a thumbnail after a current image that is a test image of a current test is created for the patient by the ultrasound diagnostic device, and a test report creation unit that automatically creates a test report on the basis of the current image and at least one past image selected by the user via the input unit from the past image displayed as the thumbnail on the display unit.

Additionally, it is preferable that the ultrasound diagnostic device measures the intima-media thickness on the basis of the test image and attaches a measurement value of the intima-media thickness to the test image, and the test report creation unit automatically creates the test report showing a measurement value of the intima-media thickness attached to the current image, a measurement value of the intima-media thickness attached to the past image, the current image, and the past image.

Moreover, it is preferable that the ultrasound diagnostic device further includes a tag creation unit that creates an information tag including the measurement value of the intima-media thickness, and a tag attachment unit that attaches the information tag created by the tag creation unit to the test image.

It is possible to adopt a configuration in which the workstation further includes a priority determination unit that gives a priority to the past image, and the workstation control unit makes the display unit display the past image as a thumbnail so as to be arranged in order of a higher priority given by the priority determination unit.

Additionally, the priority determination unit can give a higher priority to the past image to which the measurement value of the intima-media thickness is attached than the past image to which the measurement value of the intima-media thickness is not attached.

Moreover, the priority determination unit may give a higher priority to the past image of the same test part as a test part of the current image than the past image of a test part different from the test part of the current image.

Additionally, the priority determination unit may give a higher priority to the past image to which the same body mark and probe mark as a body mark and a probe mark given to the current image are given than the past image to which the same body mark and probe mark as the body mark and the probe mark given to the current image are not given.

Moreover, the priority determination unit may perform pattern matching between the past image to which the higher priority is given and the current image, and performs ranking of the priority in accordance with a level of similarity.

It is possible to adopt a configuration in which the database stores reference values of the intima-media thickness for each sex and age in advance, and the test report creation unit automatically creates the test report further showing the reference values according to the patient.

The ultrasound diagnostic device may include an elastic index calculation unit that calculates an elastic index of the blood vessel on the basis of the test image, and the test report creation unit automatically creates the test report further showing the elastic index calculated by the elastic index calculation unit.

It is possible to adopt a configuration in which the workstation control unit makes the ultrasound diagnostic device create a test image again from data before image processing before image processing for creating the past image is performed in a case where the past image to which the measurement value of the intima-media thickness is not given is present and the data before image processing is present, and the ultrasound diagnostic device attaches the measurement value of the intima-media thickness obtained by the test image created again to the test image.

Additionally, the method of controlling an ultrasound diagnostic system is a method of controlling an ultrasound diagnostic system including an ultrasound diagnostic device that transmits an ultrasound beam toward a patient from an array transducer, receives an ultrasound echo from the patient, and creates a test image of an intima-media thickness of a blood vessel, and a workstation connected to the ultrasound diagnostic device. The method comprises sequentially storing the test image created by the ultrasound diagnostic device in a database; retrieving a test image in a past test for the patient as a past image from the test image stored in the database to display the past image as a thumbnail on a display unit of the workstation after a current image that is a test image of a current test is created for the patient by the ultrasound diagnostic device; and automatically creating a test report on the basis of the current image and at least one past image selected by the user from the past image displayed as the thumbnail on the display unit.

According to the invention, provided is an ultrasound diagnostic system including the ultrasound diagnostic device that transmits the ultrasound beam toward the patient from the array transducer, receives the ultrasound echo from the patient, and creates the test image of the intima-media thickness of the blood vessel, and the workstation connected to the ultrasound diagnostic device. The ultrasound diagnostic system comprises the database that sequentially stores the test image created by the ultrasound diagnostic device. The workstation includes an input unit for allowing the user to input the various kinds of information, a display unit, the workstation control unit that retrieves the test image in the past test for the patient as the past image from the test image stored in the database to make the display unit display the past image as the thumbnail after the current image that is the test image of the current test is created for the patient by the ultrasound diagnostic device, and the test report creation unit that automatically creates the test report on the basis of the current image and at least one past image selected by the user via the input unit from the past image displayed as the thumbnail on the display unit. Thus, the test report that makes it possible to ascertain secular changes in the intima-media thickness of the blood vessel can be automatically created.

BRIEF DESCRIPTION OF THE DRAWINGS

FIG. 1 is a block diagram illustrating the configuration of an ultrasound diagnostic system related to Embodiment 1 of the invention.

FIG. 2 is a block diagram illustrating the configuration of an ultrasound diagnostic device of Embodiment 1.

FIG. 11 is a view illustrating a test report.

FIG. 14 is a block diagram illustrating the configuration of an ultrasound diagnostic system related to the modification example of Embodiment 1.

FIG. 15 is a block diagram illustrating the configuration of an ultrasound diagnostic device of Embodiment 2.

DESCRIPTION OF THE PREFERRED EMBODIMENTS

Figure 3:
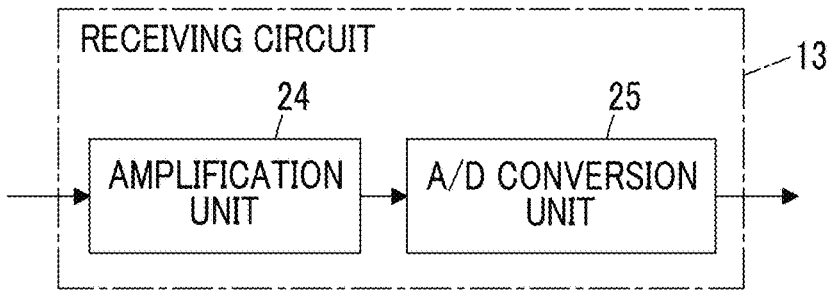
FIG. 3 is a block diagram illustrating an internal configuration of a receiving circuit.

Hereinafter, embodiments of the invention will be described with reference to the attached to drawings.

Embodiment 1

The configuration of an ultrasound diagnostic system related to Embodiment 1 of the invention is illustrated in FIG. 1. The ultrasound diagnostic system comprises an ultrasound diagnostic device 1 and a workstation 3, and the workstation 3 is connected to the ultrasound diagnostic device 1 via a connection line 2. This connection can be configured, for example, by a wired local area network (LAN), a wireless LAN, a wide area network (WAN), or other computer networks.

The ultrasound diagnostic device 1 is configured as illustrated in FIG. 2, includes an ultrasound probe 11 in which an array transducer 11A is built, and a transmitting circuit 12 and a receiving circuit 13 are connected to the array transducer 11A of the ultrasound probe 11. An image creation unit 14 is connected to the receiving circuit 13, and a display unit 16 is connected to the image creation unit 14 via a display control unit 15.

Additionally, an intima-media thickness (IMT) measurement unit 17 is connected to the image creation unit 14, the display control unit 15 is connected to the IMT measurement unit 17, and a tag attachment unit 19 is connected to the IMT measurement unit 17 via a tag creation unit 18. The tag attachment unit 19 is connected also to the image creation unit 14. Additionally, a communication unit 20 is connected to the tag creation unit 18 and the tag attachment unit 19.

A device control unit 21 is connected to the transmitting circuit 12, the receiving circuit 13, the image creation unit 14, the display control unit 15, the IMT measurement unit 17, the tag creation unit 18, the tag attachment unit 19, and the communication unit 20, respectively. Additionally, an input unit 22 and a storage unit 23 are connected to the device control unit 21, respectively.

The array transducer 11A of the ultrasound probe 11 has a plurality of elements (ultrasound transducers) that are arranged in one dimension or two dimensions. These elements transmit ultrasound waves in accordance with driving signals supplied from the transmitting circuit 12 and receive ultrasound echoes from a patient to output the received signals. The respective elements are configured, for example, using oscillators in which electrodes are formed at both ends of piezoelectric bodies including piezoelectric ceramics represented by lead zirconate titanate (PZT), polymer piezoelectric elements represented by poly vinylidene di fluoride (PVDF), and piezoelectric single crystals represented by lead magnesium niobate-lead titanate (PMN-PT).

In a case where a pulse-like or continuous-wave-like voltage is applied to the electrodes of such oscillators, piezoelectric bodies expand and contract, pulse-like or continuous-wave ultrasound waves are generated from the respective oscillators, and an ultrasound beam is formed by synthesis of those ultrasound waves. Additionally, the respective oscillators receive the propagating ultrasound waves, thereby expanding and contracting to generate electrical signals, and the electrical signals are output as received signals of the ultrasound waves.

The transmitting circuit 12 includes, for example, a plurality of pulse generators and adjusts the amounts of delay of the respective driving signals to supply the adjusted amounts of delay to the plurality of elements such that the ultrasound waves transmitted from the plurality of elements of the array transducer 11A form the ultrasound beam, on the basis of on a transmission delay pattern selected in accordance with a control signal from the device control unit 21.

As illustrated in FIG. 3, the receiving circuit 13 has a configuration in which an amplification unit 24 and an analog/digital (AD) conversion unit 25 are connected in series. The receiving circuit 13 amplifies the received signals output from the respective elements of the array transducer 11A with the amplification unit 24 and creates digital element data obtained by being AD-converted with the AD conversion unit 25.

Figure 4:
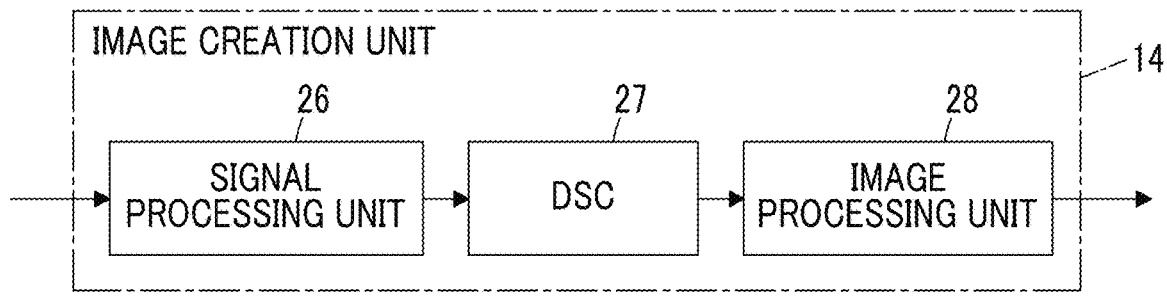
FIG. 4 is a block diagram illustrating an internal configuration of an image creation unit.

As illustrated in FIG. 4, the image creation unit 14 has a configuration in which a signal processing unit 26, a digital scan converter (DSC) 27, and an image processing unit 28 are sequentially connected in series.

The signal processing unit 26 performs reception focus processing by delaying received data output from the receiving circuit 13 in accordance with a set sonic speed on the basis of a reception delay pattern selected in accordance with the control signal from the device control unit 21, thereby performing addition (phasing addition). Sound ray signals in which the ultrasound echoes are focused are created by this reception focus processing. Moreover, the signal processing unit 26 performs correction of damping, resulting from distances in accordance with the depths of the reflection positions of the ultrasound waves, with respect to the sound ray signals, and performs envelope detection processing, thereby creating brightness-mode (B-mode) test image signals that are tomographic image information on the tissue within the patient.

Here, a test image created in a test currently performed for the patient by the ultrasound diagnostic device 1, that is, the current test, is defined as a current image. Additionally, a test image created in a test performed in the past is defined as a past image.

The DSC 27 converts the test image signals created by the signal processing unit 26 into image signals according to a scanning mode of normal television signals (raster conversion).

The image processing unit 28 outputs the test image signals to the IMT measurement unit 17, the display control unit 15, and the tag attachment unit 19 after various kinds of required image processing, such as gradation processing, is performed on the test image signals input from the DSC 27.

Figure 5:
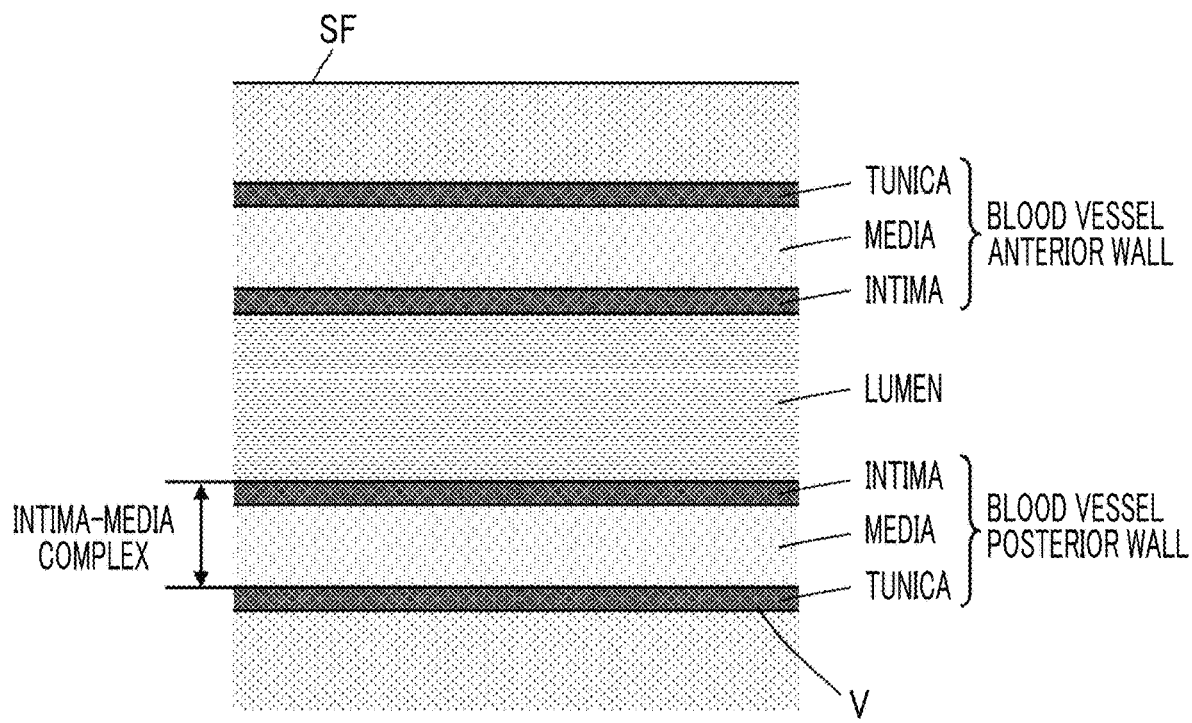
FIG. 5 is a view illustrating the configuration of an intima-media complex.

Here, the structure of a blood vessel inside a patient's body will be described with reference to FIG. 5. FIG. 5 illustrates a cross-section in a direction in which the blood vessel V extends, and a blood vessel anterior wall near a patient's body surface SF and a blood vessel posterior wall far from a patient's body surface S are illustrated in FIG. 5. These blood vessel walls are formed of three layers of an intima, a media, and a tunica, respectively, and one obtained by combining the intima and the media together is referred to as an intima-media complex.

The IMT measurement unit 17 performs image analysis of the test image signals created by the image creation unit 14 to detect the intima-media complex of the blood vessel, automatically measures the thickness of the detected intima-media complex, and outputs the measured intima-media thickness to the display control unit 15 and the tag creation unit 18. In addition, in this case, the thickness of the intima-media complex can be manually measured. For example, the display unit 16 may be made to display the test image created by the image creation unit 14 and to display a caliper on the test image, a lumen-intima boundary and a media-tunica boundary may be manually and sequentially specified, and a distance between these boundaries may be measured as the thickness of the intima-media complex.

The display control unit 15 makes the display unit 16 to display the test image on the basis of the test image signals created by the image creation unit 14. In this case, the current image that is the test image of the current test is displayed on the display unit 16. Additionally, the intima-media thickness measured by the IMT measurement unit 17 may be displayed together with the test image.

The display unit 16 includes, for example, display devices, such as a liquid crystal display (LCD) and displays the test image under the control of the display control unit 15.

The input unit 22 is for a user, for example, a doctor, or test engineer to perform an input operation and can be formed from a keyboard, a mouse, a trackball, a touch panel, and the like. Various kinds of information, such as a patient ID (identification), a patient's name, a patient's age, a patient's sex, and a test part for identifying the patient, are input to the ultrasound diagnostic device 1 via the input unit 22 by the user's input operation.

Here, a character string representing various kinds of information, such as the patient ID, the test part, a measurement value of the intima-media thickness, and a date on which the test is performed, is defined as an information tag. This information tag is for being attached to the test image, and the information included in the information tag can be associated with the test image by attaching the information tag to the test image.

The tag creation unit 18 creates the information tag on the basis of the measurement value of the intima-media thickness measured by the IMT measurement unit 17 and the various kinds of information input via the input unit 22 by the user.

The tag attachment unit 19 attaches the information tag created by the tag creation unit 18 to the test image signals created by the image creation unit 14. The test image signals are constituted of digitized data, so that the information tag constituted of the character string can be attached thereto.

The communication unit 20 connects the ultrasound diagnostic device 1 to other devices and has a function of transmitting and receiving data with respect to the connected other devices. Accordingly, the ultrasound diagnostic device 1 and the workstation 3 are connected to each other and can perform communication for transmitting and receiving various kinds of data, such as the test image.

The device control unit 21 controls the communication unit 20 and transmits the test image, to which the information tag is attached, to the workstation 3, after the information tag is attached to the test image by the tag attachment unit 19.

Additionally, the device control unit 21 performs control of the transmitting circuit 12, the receiving circuit 13, the image creation unit 14, the display control unit 15, the IMT measurement unit 17, the tag creation unit 18, and the tag attachment unit 19 on the basis of a command input to the input unit 22 by the user.

The storage unit 23 stores operating programs or the like and can be configured using a memory medium, such as a hard disk, a flexible disk, a magneto-optical (MO) disk, a magnetic tape (MT), a random access memory (RAM), a compact disk read only memory (CD-ROM), a digital versatile disk read only memory (DVD-ROM), a secure digital card (SD card), a compact flash card (CF card), or a universal serial bus memory (USB memory).

In addition, although the image creation unit 14, the display control unit 15, the IMT measurement unit 17, the tag creation unit 18, the tag attachment unit 19, and the device control unit 21 are constituted of a central processing unit (CPU) and operating programs for making the CPU perform various kinds of processing, these may be configured with a digital circuit. Additionally, the image creation unit 14, the display control unit 15, the IMT measurement unit 17, the tag creation unit 18, the tag attachment unit 19, and the device control unit 21 may be configured so as to be partially or entirely integrated into one CPU.

Figure 6:
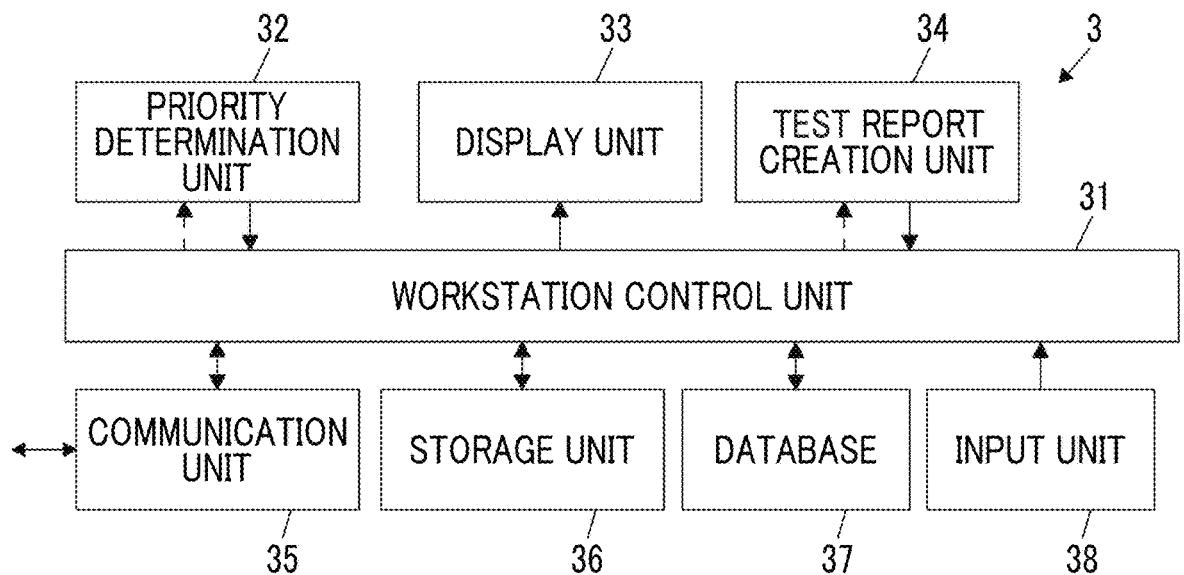
FIG. 6 is a block diagram illustrating the configuration of a workstation of Embodiment 1.

The workstation 3 is configured as illustrated in FIG. 6 and includes a workstation control unit 31. A priority determination unit 32, a display unit 33, a test report creation unit 34, a communication unit 35, a storage unit 36, a database 37, and an input unit 38 are connected to the workstation control unit 31, respectively.

The workstation 3 connects the communication unit 35 to other devices and can be configured similarly to the communication unit 20 of the ultrasound diagnostic device 1. Accordingly, communication for transmitting and receiving various kinds of data, such as the test image, can be performed between the workstation 3 and the ultrasound diagnostic device 1 via the communication unit 35.

The database 37 sequentially stores the test image transmitted from the ultrasound diagnostic device 1 and can be configured similarly to the storage unit 23 of the ultrasound diagnostic device 1. The test image created in the test performed in the past is stored as the past image in the database 37, and a test image of a patient different from a patient under testing may be stored in the database 37. Additionally, reference values of the intima-media thicknesses for each sex and age are stored in advance in the database 37.

The display unit 33 displays the test image and can be configured similarly to the display unit 16 of the ultrasound diagnostic device 1.

The input unit 38 is for the user to perform an input operation and can be configured similarly to the input unit 22 of the ultrasound diagnostic device 1. As described above, although the various kinds of information are input via the input unit 22 of the ultrasound diagnostic device 1, these various kinds of information may be input to the workstation 3 via the input unit 38.

The workstation control unit 31 performs control of the priority determination unit 32 and the test report creation unit 34 on the basis of a command input via the input unit 38 by the user.

Additionally, after the test image of the current test, that is, the current image is transmitted by the ultrasound diagnostic device 1, the workstation control unit 31 reads the information tag attached to the transmitted current image, and retrieves a past image created in a past test for the patient under testing, from the database 37, on the basis of information, such as the patient ID included in the information tag.

Figure 7:
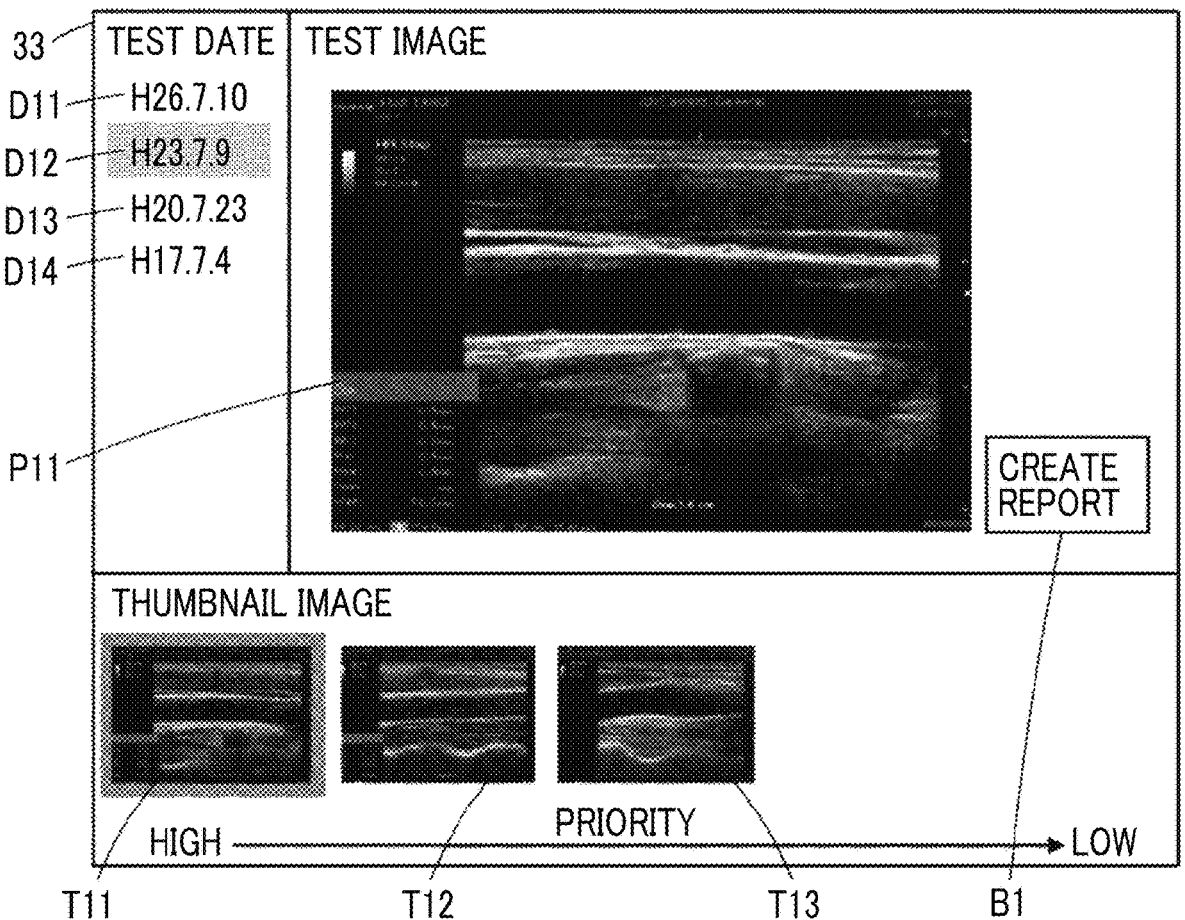
FIG. 7 is a view illustrating past images that are displayed as thumbnails in a display unit of the workstation in Embodiment 1.

Moreover, for example, as illustrated in FIG. 7, the workstation control unit 31 makes the display unit 33 display a retrieved past image P11, reduce retrieved past images so as to be aligned with the past image P11, and thumbnail-display the reduced past images as thumbnail images T11 to T13.

The priority determination unit 32 gives any priority of a high rank, a middle rank, and a low rank to the past images retrieved by the workstation control unit 31. This priority is higher in a case where there are many common points with the current image from three viewpoints of patient IDs, the presence or absence of measurement values of the intima-media thickness, and test parts, and is lower in a case where there are few common points with the current image from these viewpoints. The workstation control unit 31 can make the display unit 33 display the thumbnail images T11 to T13 in order of higher priority given to the priority determination unit 32 in this way.

The test report creation unit 34 automatically creates a test report Regarding the intima-media thickness on the basis of the current image transmitted by the ultrasound diagnostic device 1 and at least one past image selected by operating the input unit 38 by the user from the past images displayed as thumbnails on the display unit 33. Accordingly, the test report showing both the current image created in the current test and the past images created in past tests is created.

The storage unit 36 stores the operating program or the like and can be configured similarly to the storage unit 23 of the ultrasound diagnostic device 1.

In addition, although the workstation control unit 31, the priority determination unit 32, and the test report creation unit 34 are constituted of a CPU and operating programs for making the CPU perform various kinds of processing, these may be constituted of a digital circuit. Additionally, the workstation control unit 31, the priority determination unit 32, and the test report creation unit 34 may be configured so as to be partially or entirely integrated into one CPU.

Next, the operation of Embodiment 1 will be described with reference to a flowchart of FIG. 8.

First, an IMT test, that is, an intima-media thickness test, is executed in Step S1. This IMT test is executed in accordance with a flowchart of FIG. 9. In Step S21, as the user operates the input unit 22 of the ultrasound diagnostic device 1, various kinds of information, such as a patient ID, a patient's name, a patient's age, a patient's sex, and a test part, are input to the ultrasound diagnostic device 1 via the input unit 22 and are output to the tag creation unit 18 by the control of the device control unit 21. In a case where the information on the test part is input, for example, whether or not any of the carotid arteries that are respectively present on the left and right sides of the neck is a test target is input. Moreover, whether or not any of parts of blood vessels, such as a common carotid artery, an external carotid artery, an internal carotid artery, a vertebral artery, and a carotid artery bulbous portion becomes a test target is input.

In addition, as described above, the various kinds of information input via the input unit 22 may be input via the input unit 38 of the workstation 3. In this case, the various kinds of information input to the workstation 3 via the input unit 38 are transmitted to the ultrasound diagnostic device 1 via the communication unit 35. Then, the transmitted information is received by the communication unit 20 of the ultrasound diagnostic device 1 and is output to the tag creation unit 18.

In Step S22, transmission and reception and scanning of an ultrasound beam using the plurality of elements of the array transducer 11A of the ultrasound probe 11 are performed by the transmitting circuit 12 of the ultrasound diagnostic device 1, and the received signals are output from the respective elements, which have received ultrasound echoes from a patient, to the receiving circuit 13, and are amplified and AD-converted by the receiving circuit 13 to create received data.

Next, in Step S23, after the received data is input to the image creation unit 14 and is subjected to reception focus processing by the signal processing unit 26, the received data is converted into signals by the DSC 27 to create B-mode test image signals. The test image signals are output to the IMT measurement unit 17, the display control unit 15, and the tag attachment unit 19.

On the basis of the test image signals output by the image creation unit 14, in Step S24, the intima-media thickness of a blood vessel is measured by the IMT measurement unit 17. Specifically, image analysis of the test image signals is performed by the IMT measurement unit 17, a boundary between a media and a tunica illustrated in FIG. 5 is detected, and an intima-media complex located at the boundary is detected by the boundary between the intima and the lumen being detected. Then, the thickness of the detected intima-media complex is automatically measured. A measurement value of the intima-media thickness is output to the display control unit 15 and the tag creation unit 18. In addition, as described above, the display unit 16 can be made to display a test image created by the image creation unit 14 and to display a caliper on the test image, a lumen-intima boundary and a media-tunica boundary can be manually and sequentially specified, and a distance between these boundaries can be measured as the thickness of the intima-media complex.

The test image signals output by the image creation unit 14 and the intima-media thickness output by the IMT measurement unit 17 are input to the display control unit 15, and the test image created in the current test, that is, a current image, is displayed on the display unit 16. Additionally, one obtained by overlapping the measurement value of the intima-media thickness on the current image or one by arranging the measurement value of the intima-media thickness with the current image may be displayed on the display unit 16. Accordingly, the patient can be diagnosed while the user checks both the test image and the measurement value of the intima-media thickness.

Next, in Step S25, an information tag is created by the tag creation unit 18 on the basis of the measurement value of the intima-media thickness output by the IMT measurement unit 17 and the various kinds of information input to the ultrasound diagnostic device 1 via the input unit 22. Various kinds of information are included in this information tag. For example, information, such as the measurement value of the intima-media thickness, the patient ID, the patient's name, the patient's age, the patient's sex, the test part, and the date on which the test is performed, is included in this information tag.

In the subsequent Step S26, the information tag is input to the tag attachment unit 19, the test image signals output by the image creation unit 14 are input to the tag attachment unit 19, the information tag is attached to the test image signals by the tag attachment unit 19, and the test image signals are output to the communication unit 20. As described above, the information tag is a character string representing the various kinds of information, and can be attached to the digitized test image signals. In addition, although a format in which the information tag is attached to the test image signal is not limited, for example, the information tag can be attached to the test image signals in accordance with the digital imaging and communication in medicine (DICOM) format.

Moreover, in Step S27, the test image signals to which the information tag is attached are transmitted to the workstation 3 via the communication unit 20, and the transmitted test image signals are received by the communication unit 35 of the workstation 3.

Figure 8:
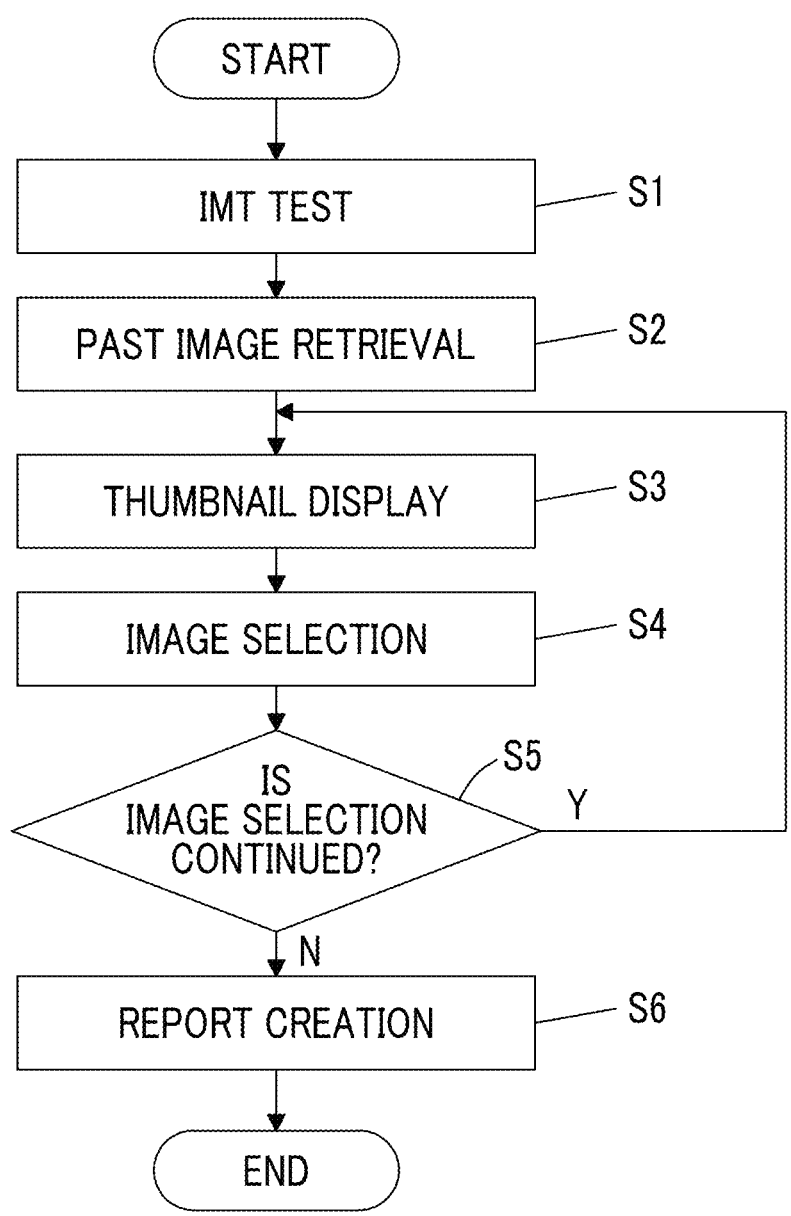
FIG. 8 is a flowchart illustrating the operation of Embodiment 1.

Next, referring back to the flowchart illustrated in FIG. 8, and in Step S2, past images stored in the database 37 are retrieved by the workstation control unit 31 of the workstation 3, and any priority of a high rank, a middle rank, and a low rank is attached to the retrieved past images by the priority determination unit 32. The retrieval and the prioritization of the past images are specifically performed in accordance with a flowchart illustrated in FIG. 10.

First, in Step S31, the information tag attached to the current image created in the current test is read by the workstation control unit 31. In the subsequent Step S32, the workstation control unit 31 reads a past image stored in the database 37 and reads an information tag attached to the read past image.

Moreover, in Step S33 the workstation control unit 31 determines whether or not a patient ID of the information tag attached to the past image is the same as the patient ID of the information tag attached to the current image. In a case where it is determined that these patient IDs are not the same, the process proceeds to Step S34 where it is determined whether or not there are any past images, which are not retrieved, in the database 37. In a case where non-retrieved past images are present in the database 37, the process returns to Step S32 and the next past image is read.

Then, in Step S33, in a case where the patient ID of the information tag attached to the current image and the patient ID of the information tag attached to the past image are the same, that is, the past image read in Step S32 is determined to be a past image created in a test performed in the past for the patient under testing, the process proceeds to Step S35.

In Step S35, whether or not the measurement value of the intima-media thickness is present in the information tag attached to the past image is determined by the workstation control unit 31. In a case where it is determined that the measurement value of the intima-media thickness is present in the information tag attached to the past image, the process proceeds to Step S36.

In Step S36, the workstation control unit 31 determines whether or not the test part of the information tag attached to the current image and the test part of the information tag attached to the past image are the same. For example, in a case where both the current images and the past image are created in tests of a left common carotid artery, it is determined that the test parts are the same and the process proceeds to Step S37. Since it is determined that this past image is common to the current image in from all three viewpoints of patient IDs, the presence or absence of measurement values of the intima-media thickness, and test parts, in Step S37, the priority of the high rank is given by the priority determination unit 32.

On the other hand, in Step S36, in a case where it is determined that the test parts of the current image and the past image are not the same, the process proceeds to Step S38 where the priority of the middle rank is given to the past image by the priority determination unit 32. Since it is determined that the current image and the past image are not common to each other from a viewpoint of test parts, a lower priority than that of the past image to which the priority is given in Step S37 is given to this past image by the priority determination unit 32.

Additionally, in Step S35, in a case where it is determined that there is no measurement value of the intima-media thickness in the information tag attached to the past image, the process proceeds to Step S39 and the priority of the low rank is attached to the past image by the priority determination unit 32. Since it is determined that the current image and the past image are not common to each other from a viewpoint of the presence or absence of measurement values of the intima-media thickness, a lower priority than that of the past image to which the priority is given in Step S38 is given to this past image by the priority determination unit 32.

In this way, after the priority of the high rank, the middle rank, or the low rank is given to the past image having the same patient ID as the current image, in Step S40, the workstation control unit 31 determines whether or not there are any past images that are not retrieved by the database 37. In a case where it is determined that non-retrieved past images are present in a database 37, the process returns to Step S32, and Step S32 to Step S40 are repeated until the retrieval of the past images stored in the database 37 is completed.

In Step S34 or Step S40, in a case where it is determined that there are no past images that are not retrieved that is, the retrieval of the past images stored in the database 37 was completed, the retrieval of the past images is completed.

In this way, as the past images of the patient under testing are automatically retrieved from the database 37 and the priority is automatically given to the retrieved past images, time and effort required to retrieve the past images from the database 37 by the user himself/herself can be effectively reduced, and quick diagnosis can be performed.

After the image retrieval by the workstation control unit 31 is completed, the process returns to the flowchart illustrated in FIG. 8, and in the subsequent Step S3, as illustrated in FIG. 7, the workstation control unit 31 makes the display unit 33 display the retrieved past images as the thumbnail images T11 to T13. The thumbnail images T11 to T13 are arranged in order in which the priority given to the past images by the priority determination unit 32 is higher, that is, in order in which there are many common points with the current image from three viewpoints of patient IDs, the presence or absence of measurement values of the intima-media thickness, and test parts.

Additionally, dates on which the respective past images are created are displayed to be aligned sequentially from the new one on the display unit 33, and a date D11 on which the newest past image is created is displayed at the top. In a case where the input unit 38 of the workstation 3 or the input unit 22 of the ultrasound diagnostic device 1 is operated by the user, for example, a date D12 is selected, the date D12 is highlighted of by the workstation control unit 31, and past images corresponding to the date D12 are displayed as thumbnails.

In the subsequent Step S4, any of the thumbnail images T11 to T13 is selected by the user. For example, in a case where the thumbnail image T11 is selected, the thumbnail image T11 is highlighted by the workstation control unit 31. In this case, since the thumbnail images T11 to T13 are arranged in order of higher priority, the user can easily select a thumbnail image corresponding to a past image with many common points with the current image, and it is possible to speed up diagnosis more effectively.

Additionally, a past image corresponding to the selected thumbnail image T11 is displayed on the display unit 33 as the past image P11, and the user can determine whether or not the past image P11 displayed on the display unit 33 is used for a test report.

In the subsequent Step S5, in a case where it is determined that image selection is continued by the user, the process returns to Step S3 and a past image is selected through Step S3 and Step S4. Accordingly, for example, after a past image of a right common carotid artery is selected, a past image of the left common carotid artery can be further selected. In this way, at least one past image is selected by the user through Step S3 to Step S5.

Then, in Step S5, in a case where the user determines that the image selection is not continued, that is, the selection of the past images to be used for the test report is completed, and a report generation execution button B1 displayed on the display unit 33 is selected, the test report R as illustrated in FIG. 11 is automatically created by the test report creation unit 34. Specifically, the information tag attached to the current image and the information tag attached to the selected past image are read, respectively, reference values of the intima-media thickness for each sex and each age stored in the database 37 are read, and the test report R is automatically created on the basis of these kinds of read information.

The test report R shows test results of the intima-media thickness, and the user can make the patient view the test report R and explain the test results and diagnostic results. The user may make the display unit 33 display the test report R and make the patient the test report R, or may print the test report R to deliver the test report R to the patient as long as a printer is connected to the workstation 3. The test report R includes a patient identification field F1 showing information for identifying the patient, a test result field F2 showing the test results, a graph field F3 showing a graph of the test results, a test image field F4 showing test images of the intima-media thickness, an outline field F5 showing the outline of the results, and a comment field F6 showing comments by the user.

A patient ID, a patient's name, a patient's sex, and a patient's age are shown in the patient identification field F1. Additionally, a test date, a test part, the greatest intima-media thickness (MAX IMT) and the presence or absence of plaque of a right artery and the greatest intima-media thickness and the presence or absence of plaque of a left artery are shown in the test result field F2. These kinds of information are included in an information tag.

A graph G of the test results having the greatest intima-media thickness on the vertical axis and having the age on the horizontal axis is displayed on the graph field F3. This graph G corresponds to the test results shown in the test result field F2, and a reference range between an upper limit value and a lower limit value of reference values of the intima-media thickness corresponding to the patient's age and sex, are illustrated in addition to the test results. It can be seen that test results of a current test and a previous test are shown together on the graph G and the current test result exceeds the upper limit of the reference range corresponding to the patient's age.

Test images of the intima-media thickness of left and right carotid arteries in a current test and test images of the intima-media thickness of the left and right carotid arteries in a previous test are respectively shown in the test image field F4. Additionally it is illustrated in the outline field F5 whether or not the current test results exceed the reference range of the intima-media thickness. Moreover, "There is a possibility that arteriosclerosis is progressing" and comments corresponding to previous test results and the current test results are shown in the comment field F6. The outline field F5 and the comment field F6 may be automatically entered so as to correspond to the test results, or may be entered by the operation of the user.

In this way, since the current test results and the previous test results are shown together by the test report R, secular changes in the intima-media thickness of the patient under testing can be easily ascertained. Additionally, as described above, in a case where a past image corresponding to the current image is automatically retrieved and the user selects the past image, the test report R that allows the secular changes in intima-media thickness to be ascertained is automatically created. Accordingly, it is possible to quickly perform diagnosis without requiring time and effort for the creation of the test report R.

In addition, although a test report in which the reference range of the intima-media thickness corresponding to the patient's age and sex is not shown may be created, it is easy to diagnose the user in a case where the reference range is shown as in the graph G of the graph field F3. Therefore, it is preferable that the reference range is shown.

Additionally, in Step S3 to Step S5 of the flowchart illustrated in FIG. 8, past images created on two or more different dates may be selected. As a result, for example, test results are reflected in a field "test before last" of the test result field F2 of the test report R illustrated in FIG. 11, and the current test results are also reflected in the graph G of the graph field F3. Accordingly, it is possible to ascertain secular changes in the intima-media thickness of the patient under testing in more detail.

Figure 9:
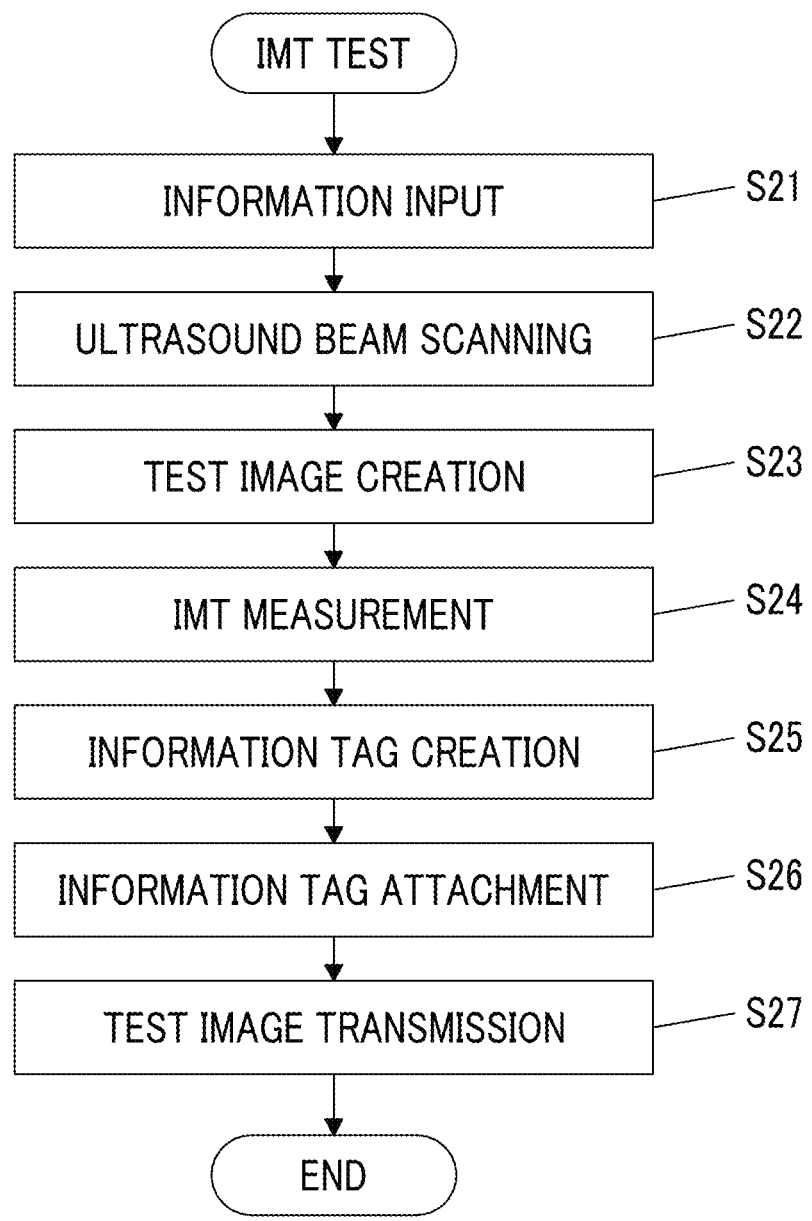
FIG. 9 is a flowchart illustrating an intima-media thickness test in Embodiment 1.

Moreover, in Step S2 of the flowchart illustrated in FIG. 8, in a case where a plurality of current images are created in the current test prior to the retrieval of the past images, the user may select the current images. For example, in the current test, in a case where Steps S21 to S27 of the flowchart illustrated in FIG. 9 are repeated, for example, a current image of the intima-media thickness of the right common carotid artery is created, and a current image of the intima-media thickness of the left common carotid artery is continuously created. Then, these current images are transmitted from the ultrasound diagnostic device 1 to the workstation 3 and are sequentially stored in the database 37.

Figure 12:
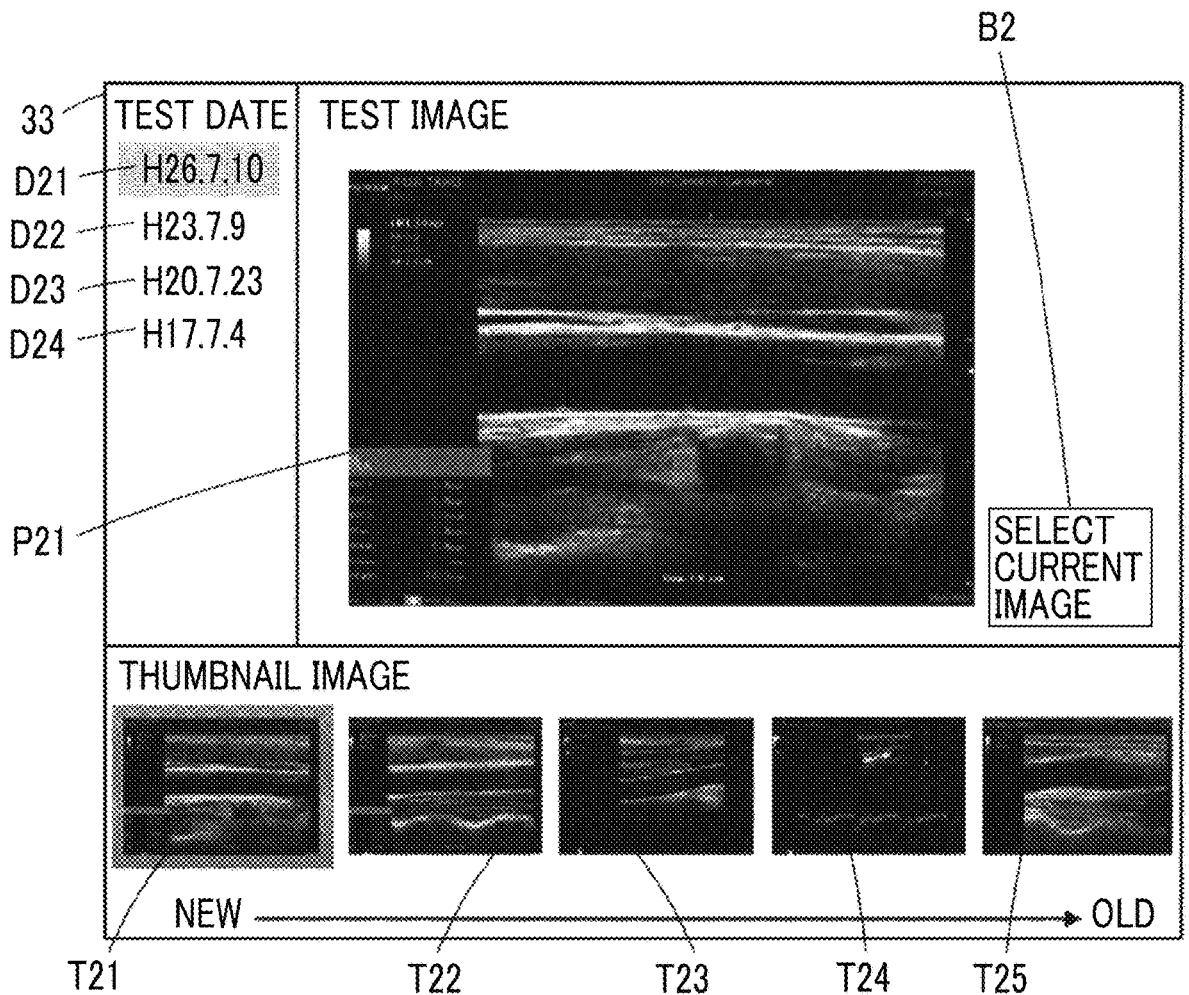
FIG. 12 is a view illustrating current images that are displayed as thumbnails in a display unit of a workstation in a modification example of Embodiment 1.

As illustrated in FIG. 12, the plurality of current images created in the current test are displayed as thumbnails on the display unit 33 by the control of the workstation control unit 31, and a current image that the user uses for retrieval of a past image can be selected from these current images. Accordingly, in a case where the plurality of current images are created in the current test, the user can freely select a current image. For example, as the display unit 33 is made to display thumbnail images T21 to T25 so as to be sequentially arranged from those that are newly created and the user selects the thumbnail images T21 to T25 and selects a current image selection button B2, the user can select a current image. Then, a past image can be retrieved on the basis of the current image selected by the user.

Figure 10:
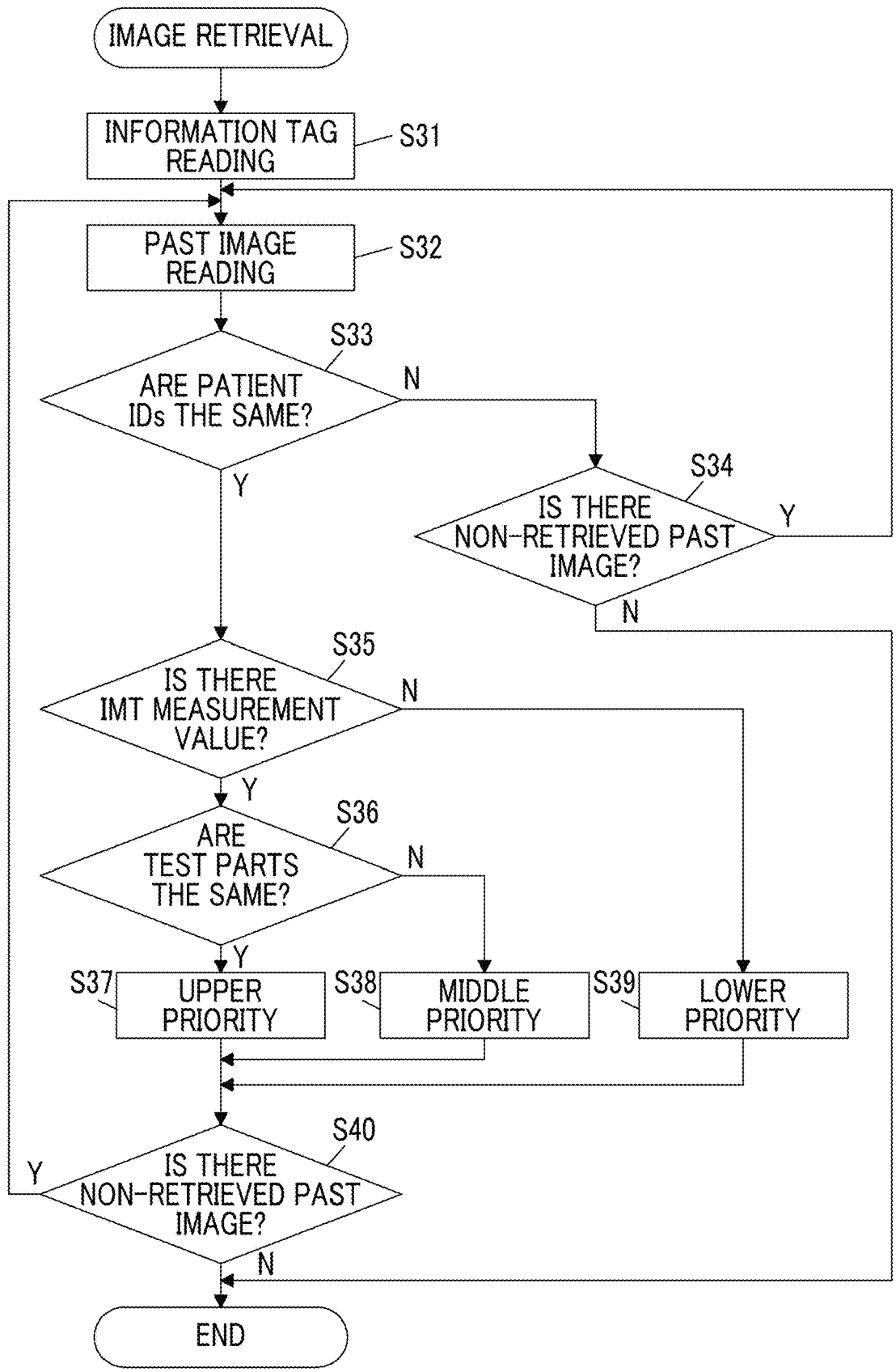
FIG. 10 is a flowchart illustrating image retrieval in Embodiment 1.
Figure 13:
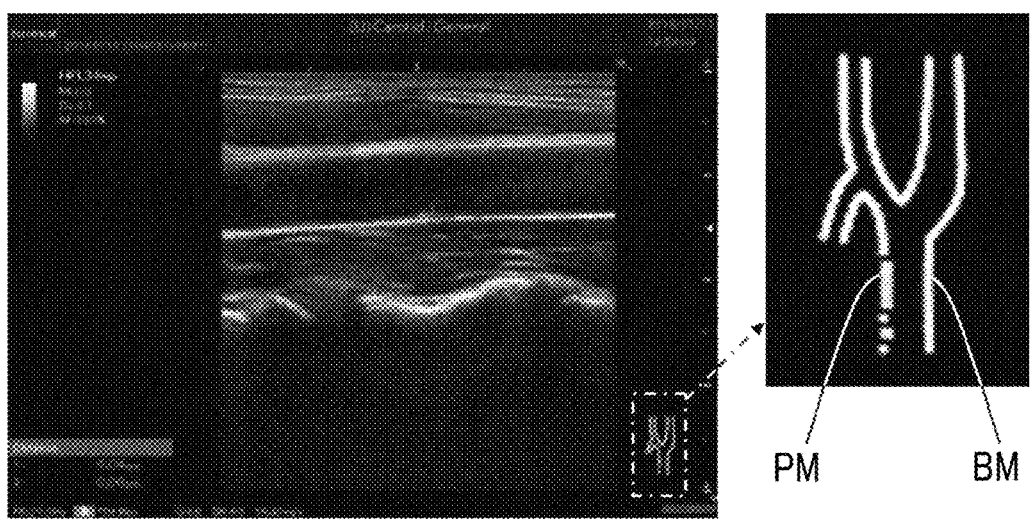
FIG. 13 is a view illustrating an example of a body mark and a probe mark.

In addition, in Step S36 of the flowchart illustrated in FIG. 10, in a case where a body mark BM and a probe mark PM that are illustrated in FIG. 13 are given to the current image, priority may be given to the past image with reference to these marks. By determining whether or not the body mark BM and the probe mark PM given to the current image, and a body mark BM and a probe mark PM given to the past image are the same, it is possible to more exactly determine whether or not the test parts of the current image and the past image are the same. Additionally, since the test parts can be easily determined, quick determination of the test parts is possible.

Additionally, in Step S3 of the flowchart illustrated in FIG. 8, in a case where the past images retrieved by the workstation control unit 31 are displayed as thumbnails on the display unit 33, pattern matching may be performed on a past image to which the priority of a high rank is given in Step S37 of the flowchart illustrated in FIG. 10 and the current image, so that past images with higher similarity (correlation coefficient) are sequentially arranged. Particularly, the pattern matching may be performed on the past images and the current image after binarization processing such that a blood vessel region and its peripheral tissue can be separated from each other.

Additionally, in Step S33 of the flowchart illustrated in FIG. 10, although it is determined whether or not the patient ID of the information tag attached to each past image is the same as the patient ID of the information tag attached to the current image, whether or not patient's names are the same may be determined.

In addition, as illustrated in FIG. 14, the ultrasound diagnostic device 1 and the workstation 3 may be connected to each other via a network N. The network N can be constituted of a wired LAN, a wireless LAN, a WAN, or other computer networks. The test images may be sequentially stored in a server SV connected to the Network N instead of the database 37 of the workstation 3.

Additionally, the server SV can be used as a common database by connecting an ultrasound diagnostic device separate from the ultrasound diagnostic device 1 and a workstation separate from the separate workstation 3 to the network N. Moreover, by storing reference values of the intima-media thickness for each sex and each age in advance in the server SV, the reference values can be commonly used.

Embodiment 2

In the above-described Embodiment 1, the IMT measurement unit 17 of the ultrasound diagnostic device 1 measures the intima-media thickness on the basis of the test images of the intima-media thickness of a blood vessel. However, Moreover, the elastic index of a blood vessel may be calculated on the basis of the test images of the intima-media thickness and a test report may be created on the basis of the elastic index of the blood vessel and the measurement value of the intima-media thickness. Here, the elastic index of the blood vessel means, for example, a blood vessel change rate, a stiffness parameter, a strain, and an elastic modulus.

The configuration of an ultrasound diagnostic device 4 of Embodiment 2 is illustrated in FIG. 15. The ultrasound diagnostic device 4 of Embodiment 2 further includes a blood vessel elasticity calculation unit 41 in the configuration of the ultrasound diagnostic device 1 of Embodiment 1 illustrated in FIG. 2, and the blood vessel elasticity calculation unit 41 is connected to the image creation unit 14, the display control unit 15, and the tag creation unit 18.

The blood vessel elasticity calculation unit 41 performs the image analysis of the test image signals created by the image creation unit 14 to calculate the elastic index of the blood vessel and outputs the measured elastic index of the blood vessel to the display control unit 15 and the tag creation unit 18.

In a case where the test image signals created by the image creation unit 14 are input to the blood vessel elasticity calculation unit 41, the elastic index of the blood vessel is calculated by the image analysis of the test image signals being performed by the blood vessel elasticity calculation unit 41, and the calculated elastic index of the blood vessel is output to the display control unit 15 and the tag creation unit 18. In addition, the elastic index of the blood vessel can also be calculated using data before image processing for creating the test image signals. Accordingly, the elastic index of the blood vessel can be calculated with higher accuracy.

In a case where the calculated elastic index of the blood vessel is input to the display control unit 15, the elastic index and the test images of the blood vessel are displayed on the display unit 16. Additionally, an information tag including information on the calculated elastic index of the blood vessel is created by the tag creation unit 18 and is output to the tag attachment unit 19, and the information tag is attached to the test image signals by the tag attachment unit 19. Then, the test images are transmitted from the ultrasound diagnostic device 4 to the workstation 3 and are sequentially stored in the database 37.

In a case where the test report R is created by the test report creation unit 34 of the workstation 3 on the basis of the test images stored in the database 37, the information on the elastic index of the blood vessel included in the information tag is reflected in the test report R. The test report R created in this way further shows the elastic index of the blood vessel and the test results of the intima-media thickness in addition to the test results of the intima-media thickness. For this reason, it is possible to diagnose the patient in more detail on the basis of the test report R.

In addition, the reference range of the elastic index of the blood vessel corresponding to the patient's age and sex may be stored in advance in the database 37, and the reference range of the elastic index of the blood vessel may be shown in the test report R. Accordingly, since it is easy for the user to diagnose the patient, this is preferable.

Embodiment 3

In the above-described Embodiment 1 and Embodiment 2, an information tag including a measurement value of the intima-media thickness of a blood vessel stored in the database 37 may not be attached to the past image. In Embodiment 3, in a case where the past image to which the information tag including the measurement value of the intima-media thickness of the blood vessel is not attached is stored in the database 37, data before image processing for creating this past image is retrieved from the database 37. Then, in a case where the data before image processing is present, a past image is again created, and the intima-media thickness is measured on the basis of the past image that is created again.

Figure 16:
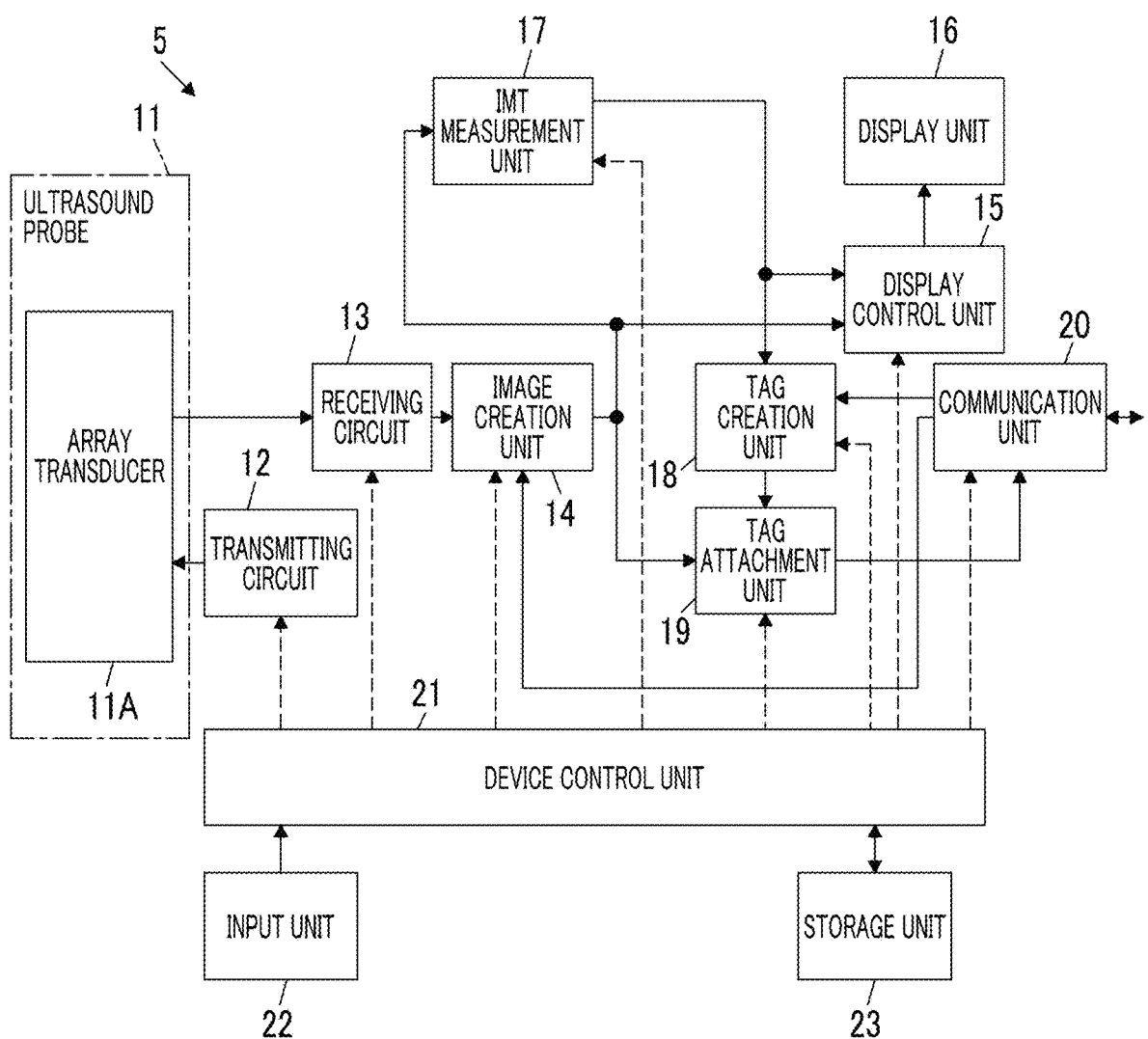
FIG. 16 is a block diagram illustrating the configuration of an ultrasound diagnostic device of Embodiment 3.

The configuration of an ultrasound diagnostic device 5 of Embodiment 3 is illustrated in FIG. 16. In the ultrasound diagnostic device 5 of Embodiment 3, the communication unit 20 and the image creation unit 14 are connected to each other in the configuration of the ultrasound diagnostic device 1 of Embodiment 1 illustrated in FIG. 2.

Figure 17:
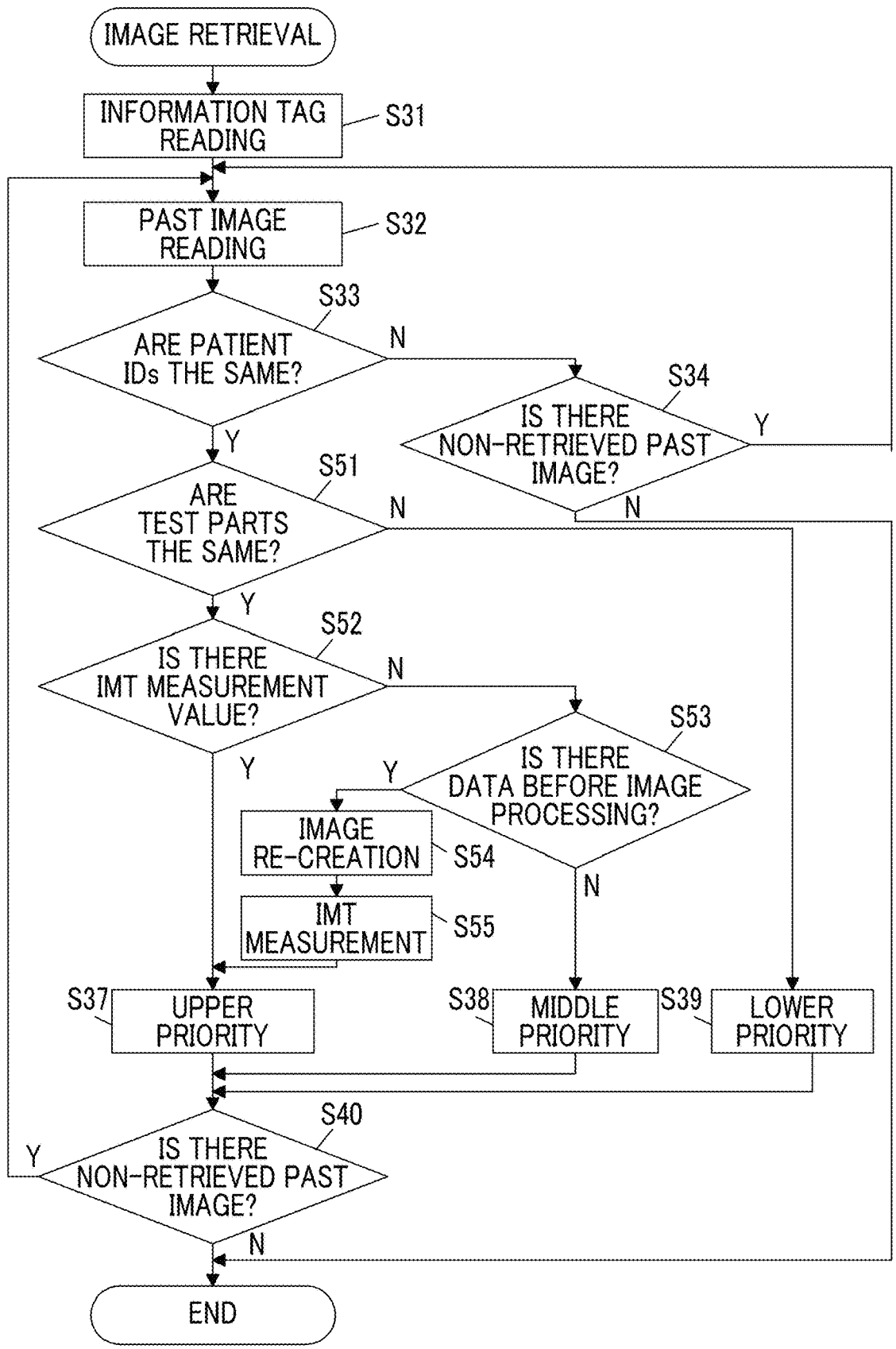
FIG. 17 is a flowchart illustrating image retrieval in Embodiment 3.

Next, the operation of Embodiment 3 will be described with reference to a flowchart of FIG. 17.

First, in Step S31, an information tag attached to a current image is read by the workstation control unit 31 of the workstation 3 of Embodiment 3, and in the subsequent Step S32, and a past image stored in the database 37 is read. Then, in Step S33, in a case where the workstation control unit 31 determines that patient IDs of information tags attached to the current image and the past image are the same as each other, the process proceeds to Step S51.

In Step S51, in a case where the workstation control unit 31 determines that a test part of the information tag attached to the current image and a test part of the information tag attached to the past image are the same, the process proceeds to Step S52. In Step S52, whether or not a measurement value of the intima-media thickness is present in the information tag attached to the past image is determined by the workstation control unit 31. In Step S52, in a case where it is determined that the measurement value of the intima-media thickness is not present in the information tag attached to the past image, the process proceeds to Step S53.

In the subsequent Step S53, the data before image processing for creating this past image is retrieved from the database 37 by the workstation control unit 31. In a case where it is determined that the data before image processing is present, the process proceeds to Step S54. Then, in Step S54, the retrieved data before image processing is transmitted from the workstation 3 to the ultrasound diagnostic device 5 and is output from the communication unit 20 to the image creation unit 14 by the control of the device control unit 21. A past image is again created from the data before image processing by the image creation unit 14 by keeping imaging conditions, such as a gain, in line with the current image, and the past image that is created again is output to the IMT measurement unit 17 and the tag attachment unit 19.

In the subsequent Step S55, the intima-media thickness of the blood vessel is measured on the basis of the re-created past image by the IMT measurement unit 17 and is output to the tag creation unit 18, and an information tag including a measurement value of an intima-media thickness is created by the tag creation unit 18 and is output to the tag attachment unit 19. The tag attachment unit 19 attaches the information tag created by the tag creation unit 18 to the past image created again by the image creation unit 14. This past image is output to the communication unit 20 and is further transmitted to the workstation 3, and the process proceeds to Step S37.

The information tag including the measurement value of the intima-media thickness is attached to the test image created again and is common to the current image in all the three viewpoints of patient IDs, the presence or absence of measurement values of the intima-media thickness, and test parts. For this reason, in Step S37, the priority of a high rank is given by the priority determination unit 32 of the workstation 3.

Accordingly, even in a case where information on a measurement value of the intima-media thickness is not attached to a past image, a test image can be again created from the data before image processing corresponding to this past image and the measurement value of the intima-media thickness can be acquired. Therefore, the test report R can be created without actuating the ultrasound diagnostic device 5 again for the patient.

In addition, the past image created again is stored in the database 37 by the control of the workstation control unit 31 after priority is given by the priority determination unit 32.

In Embodiments 1 to 3, although the ultrasound diagnostic systems create the test report on the basis of the current image and the past images retrieved by workstation, the invention is not limited to this and an ultrasound diagnostic system may be configured so as to create a test report only on the basis of the current image.

That is, this ultrasound diagnostic system is an ultrasound diagnostic system comprising an ultrasound diagnostic device that transmits an ultrasound beam toward a patient from an array transducer, receives an ultrasound echo from the patient, and creates test images of an intima-media thickness of a blood vessel, and a workstation connected to the ultrasound diagnostic device. The ultrasound diagnostic system comprises a database that sequentially stores the test images created by the ultrasound diagnostic device. The workstation includes an input unit for allowing a user to input various kinds of information, a display unit, a workstation control unit that stores current images in the database and makes the display unit display the current images stored in the database as thumbnails, after the current images that are test images of a current test are created for the patient by the ultrasound diagnostic device, and a test report creation unit that automatically creates a test report on the basis of at least one current image selected by the user via the input unit from the current images displayed as the thumbnails on the display unit.

Accordingly, the test images created by the ultrasound diagnostic device are sequentially stored in the database of the workstation, and the test report can be easily created on the basis of the stored test images.

EXPLANATION OF REFERENCES 1, 4, 5: ultrasound diagnostic device
2: connection line
3: workstation
11: ultrasound probe
11A: array transducer
12: transmitting circuit
13: receiving circuit
14: image creation unit
15: display control unit
16, 33: display unit
17: IMT measurement unit
18: tag creation unit
19: tag attachment unit
20, 35: communication unit
21: device control unit
22, 38: input unit
23, 36: storage unit
24: amplification unit
25: AD conversion unit
26: signal processing unit
27: DSC
28: image processing unit
31: workstation control unit
32: priority determination unit
34: test report creation unit
37: database
41: blood vessel elasticity calculation unit
N: network
SV: server
SF: body surface
V: blood vessel
P11: past image
P21: current image
T11 to T13, T21 to T25: thumbnail images
D11 to D14, D21 to D24: date
B1: report generation execution button
B2: current image selection button
BM: body mark
PM: probe mark
R: test report
F1: patient identification field
F2: test result field
F3: graph field
F4: test image field
F5: outline field
F6: comment field
G: graph

What is claimed is:

1. An ultrasound diagnostic system comprising:
an array transducer,
a transmitting circuit configured to transmit an ultrasound beam from the array transducer,
a receiving circuit configured to receive an ultrasound echo,
a database configured to store a first set of ultrasound images of past tests for any patients including a first patient, where each ultrasound image of the first set of ultrasound images of the past tests have attached patient IDs corresponding to the any patients and include at least one ultrasound image on which an intima-media thickness measurement of a vessel is performed in any test parts,
a display device, and
one or more processors configured to
create a first ultrasound image including a first vessel in a first test part of the first patient of a current test based on the ultrasound echo received by the receiving circuit,
attach a first patient ID corresponding to the first patient to the first ultrasound image,
measure an intima-media thickness of the first vessel based on the first ultrasound image,
determine, for each ultrasound image of the first set of ultrasound images of the past tests stored in the database, whether a first condition representing that the ultrasound image has the first patient ID is satisfied, whether a second condition representing that the measurement of the intima-media thickness is performed on the ultrasound image is satisfied, and whether a third condition representing that the ultrasound image includes the first test part is satisfied,
determine and attach priorities corresponding to the each ultrasound image of the first set of ultrasound images stored in the database where higher priority is attached to at least one first ultrasound image of the first set of ultrasound images satisfying more conditions among the first condition, the second condition and the third condition, make the display device display the first set of ultrasound images in a first arrangement order which is determined based on a decreasing priority, receive a selection of at least one image of the at least one ultrasound image from the database on which the measurement of the intima-media thickness is performed, from the first set of ultrasound images by a user, receive a report generation instruction from the user, and upon receiving the report generation instruction, automatically create a single test report image including the first ultrasound image, the at least one image selected by the user, the measurement result of the intima-media thickness corresponding to the first ultrasound image and at least one measurement result of the intima-media thickness corresponding to the at least one image selected by the user.

2. The ultrasound diagnostic system according to claim 1, wherein the one or more processors are configured to receive the selection of the at least one image by the user as the report generation instruction.

3. The ultrasound diagnostic system according to claim 1, wherein the first set of ultrasound images includes second ultrasound images of a same test part as the first test part of the first ultrasound image and third ultrasound images of a different test part from the first test part, and the one or more processors are further configured to determine the priorities to give higher priorities to the second ultrasound images than priorities of the third ultrasound images.

4. The ultrasound diagnostic system according to claim 1, wherein the first set of ultrasound images includes fourth ultrasound images having a same body mark and a same probe mark as a current body mark and a current probe mark given to the first ultrasound image and fifth ultrasound images not having the same body mark and the same probe mark as the current body mark and the current probe mark, and the one or more processors are further configured to determine the priorities to give higher priorities to the fourth ultrasound images than priorities of the fifth ultrasound images.

5. The ultrasound diagnostic system according to claim 1, wherein the one or more processors are further configured to perform pattern matching between the first set of ultrasound images and the first ultrasound image to acquire similarities between the first set of ultrasound images and the first ultrasound image, and determine the priorities so that the priorities corresponding to the first set of ultrasound images having the similarities with higher values to be higher.

6. The ultrasound diagnostic system according to claim 1, wherein the database is configured to store reference values of the intima-media thickness for each sex and age in advance, and the one or more processors are configured to automatically create the single test report image further comprising the reference values according to the patient.

7. The ultrasound diagnostic system according to claim 1, wherein the one or more processors are configured to calculate an elastic index of the blood vessel based on the ultrasound images of the intima-media thickness of the blood vessel, and automatically create the single test report image further comprising the elastic index.

8. The ultrasound diagnostic system according to claim 1, wherein the one or more processors configured to attach higher priority to the at least one first ultrasound image of the first set of ultrasound images satisfying all of the first, second, and third conditions, attach middle priority to at least one second ultrasound image of the first set of ultrasound images satisfying two of the first, second, and third conditions, and attach lower priority to at least one third ultrasound image of the first set of ultrasound images satisfying one of the first, second, and third conditions.

9. The ultrasound diagnostic system according to claim 2, wherein the one or more processors are configured to create an information tag including the measurement result of the intima-media thickness, and attach the information tag to the first ultrasound image.

10. The ultrasound diagnostic system according to claim 2, wherein the first set of ultrasound images includes second ultrasound images of a same test part as the first test part of the first ultrasound image and third ultrasound images of a different test part from the first test part, and the one or more processors are further configured to determine the priorities to give higher priorities to the second ultrasound images than priorities of the third ultrasound images.

11. The ultrasound diagnostic system according to claim 2, wherein the first set of ultrasound images includes fourth ultrasound images having a same body mark and a same probe mark as a current body mark and a current probe mark given to the first ultrasound image and fifth ultrasound images not having the same body mark and the same probe mark as the current body mark and the current probe mark, and the one or more processors are further configured to determine the priorities to give higher priorities to the fourth ultrasound images than priorities to the fifth ultrasound images.

12. The ultrasound diagnostic system according to claim 2, wherein the one or more processors are configured to perform pattern matching between the first set of ultrasound images and the first ultrasound image to acquire similarities between the first set of ultrasound images and the first ultrasound image, and determine the priorities so that the priorities corresponding to the first set of ultrasound images having the similarities with higher values to be higher.

13. The ultrasound diagnostic system according to claim 2, wherein in a case where data before image processing acquired in any one of the past tests are stored in the database, the one or more processors are further configured to create a new ultrasound image from the data before image processing, and measure the intima-media thickness based on the new ultrasound image to acquire a new measurement value, and attach the new measurement value to the new ultrasound image.

14. The ultrasound diagnostic system according to claim 9, wherein the first set of ultrasound images includes fourth ultrasound images having a same body mark and a same probe mark as a current body mark and a current probe mark given to the first ultrasound image and fifth ultrasound images not having the same body mark and the same probe mark as the current body mark and the current probe mark, and the one or more processors are further configured to determine the priorities to give higher priorities to the fourth ultrasound images than priorities of the fifth ultrasound images.

15. The ultrasound diagnostic system according to claim 9, wherein the one or more processors are configured to perform pattern matching between the first set of ultrasound images and the first ultrasound image to acquire similarities between the first set of ultrasound images and the first ultrasound image, and determine the priorities so that the priorities corresponding to the first set of ultrasound images having the similarities with higher values to be higher.

16. A method of controlling an ultrasound diagnostic system comprising:

storing a first set of ultrasound images of past tests for any patients including a first patient in a database, where each ultrasound image of the first set of ultrasound images of the past tests have attached patient IDs corresponding to the any patients and include at least one ultrasound image on which an intima-media thickness measurement of a vessel is performed in any test parts;

transmitting an ultrasound beam from an array transducer;

receiving an ultrasound echo;

creating a first ultrasound image including a first vessel in a first test part of the first patient of a current test based on the ultrasound echo;

attaching a first patient ID corresponding to the first patient to the first ultrasound image;

measuring an intima-media thickness of the first vessel based on the first ultrasound image;

determining, for each ultrasound image of the first set of ultrasound images of the past tests stored in the database, whether a first condition representing that the ultrasound image has the first patient ID is satisfied, whether a second condition representing that the measurement of the intima-media thickness is performed on the ultrasound image is satisfied, and whether a third condition representing that the ultrasound image includes the first test part is satisfied;

determining and attaching priorities corresponding to the each ultrasound image of the first set of ultrasound images stored in the database where higher priority is attached to at least one first ultrasound image of the first set of ultrasound images satisfying more conditions among the first condition, the second condition and the third condition;

displaying the first set of ultrasound images in a first arrangement order which is determined based on a decreasing priority;

receiving a selection of at least one image of the at least one ultrasound image from the database on which the measurement of the intima-media thickness is performed, from the first set of ultrasound images by a user via an input device;

receiving a report generation instruction from the user via the input device;

upon accepting the report generation instructions, automatically creating a single test report image including the first ultrasound image, the at least one image selected by the user, the measurement result of the intima-media thickness corresponding to the first ultrasound image and at least one measurement result of the intima-media thickness corresponding to the at least one image selected by the user.

\* \* \* \* \*